(12) United States Patent
Nakayama et al.

(10) Patent No.: US 7,863,081 B2
(45) Date of Patent: Jan. 4, 2011

(54) FIELD EFFECT TRANSISTOR AND METHOD OF MANUFACTURING THE SAME

(75) Inventors: Tomonari Nakayama, Yokohama (JP); Daisuke Miura, Numazu (JP)

(73) Assignee: Canon Kabushiki Kaisha, Tokyo (JP)

( * ) Notice: Subject to any disclaimer, the term of this patent is extended or adjusted under 35 U.S.C. 154(b) by 185 days.

(21) Appl. No.: 10/556,184

(22) PCT Filed: Aug. 26, 2004

(86) PCT No.: PCT/JP2004/012684

§ 371 (c)(1), (2), (4) Date: Nov. 9, 2005

(87) PCT Pub. No.: WO2005/022650

PCT Pub. Date: Mar. 10, 2005

(65) Prior Publication Data

US 2006/0211180 A1    Sep. 21, 2006

(30) Foreign Application Priority Data

Aug. 28, 2003 (JP) ............... 2003-305485

(51) Int. Cl.
*H01L 21/00* (2006.01)
*H01L 51/30* (2006.01)

(52) U.S. Cl. ............... 438/82; 438/99; 257/40; 257/E51.04; 257/E51.005; 257/E51.001; 313/499; 313/506; 430/200; 430/201

(58) Field of Classification Search ............... 438/82, 438/99; 257/40, E51.041, E51.005, E51.001, 257/E51.006; 313/499, 506; 430/200, 201; *H01L 51/30, H01L 51/40, 21/00, 51/00, 35/24*
See application file for complete search history.

(56) References Cited

U.S. PATENT DOCUMENTS

| 5,596,208 A | 1/1997 | Dodabalapur et al. ......... 257/66 |
| 6,905,907 B2 * | 6/2005 | Konuma ..................... 438/99 |
| 7,094,625 B2 | 8/2006 | Miura et al. |
| 7,193,237 B2 * | 3/2007 | Aramaki et al. ............... 257/40 |

(Continued)

FOREIGN PATENT DOCUMENTS

EP    0 716 459 A2    6/1996

(Continued)

OTHER PUBLICATIONS

PCT Notification of Transmittal of International Preliminary Report on Patentability (PCT RULE 71.1), date mailed Dec. 20, 2005 of International Application No. PCT/JP2004/012684. (Form PCT/IPEA/416).

(Continued)

*Primary Examiner*—Hsien-ming Lee
(74) *Attorney, Agent, or Firm*—Fitzpatrick, Cella, Harper & Scinto

(57) ABSTRACT

Provided is a field effect transistor having an organic semiconductor layer, in which crystal grains having a maximum diameter of 10 μm or more account for 25% or more of the surface area of the organic semiconductor layer. The organic semiconductor layer preferably contains 7 to 200 crystal grains having a maximum diameter of 10 μm or more per 0.01 $mm^2$. The organic semiconductor layer preferably contains a porphyrin crystal.

2 Claims, 3 Drawing Sheets

U.S. PATENT DOCUMENTS

| | | |
|---|---|---|
| 7,285,441 B2 | 10/2007 | Miura et al. |
| 7,394,096 B2 | 7/2008 | Miura et al. |
| 7,435,989 B2 | 10/2008 | Nakayama et al. |
| 2001/0015438 A1 | 8/2001 | Callegari et al. ............ 257/40 |
| 2005/0202348 A1 | 9/2005 | Nakayama et al. |
| 2006/0214159 A1 | 9/2006 | Nakayama et al. |
| 2007/0012914 A1 | 1/2007 | Miura et al. |
| 2007/0096079 A1 | 5/2007 | Nakayama et al. |
| 2008/0277649 A1 | 11/2008 | Masumoto et al. |

FOREIGN PATENT DOCUMENTS

| | | |
|---|---|---|
| EP | 0 716 459 A3 | 6/1996 |
| JP | 5-110069 A | 4/1993 |
| JP | 5-152560 A | 6/1993 |
| JP | 8-228034 | 9/1996 |
| JP | 2000-269515 | 9/2000 |
| JP | 2003-304014 A | 10/2003 |
| JP | 2004-6750 A | 1/2004 |
| JP | 2004-323376 | 11/2004 |

OTHER PUBLICATIONS

PCT International Preliminary Report on Patentability (PCT Article 36 Rule 70) date mailed Dec. 21, 2005 of International Application No. PCT/JP2004/012684. (Form PCT/IPEA/416).

H. Sirringhaus et al., "Two-Dimensional Charge Transport in Self-Organized, High-Mobility Conjugated Polymers," 401 Nature 685-687 (Oct. 1999).

Peter T. Herwig et al., "A Soluble Pentacene Precursor: Synthesis, Solid-State Conversion into Pentacene and Application in a Field-Effect Transistor," 11 Advanced Materials 480-483 (1999).

Uno, et al., "Synthesis of Conjugation-expanded Porphyrins Based on the Retro Diels-Alder Reaction", Journal of Synthetic Organic Chemistry, vol. 60, No. 6, Jun. 2002, pp. 581-592.

* cited by examiner

FIELD EFFECT TRANSISTOR AND METHOD OF MANUFACTURING THE SAME

TECHNICAL FIELD

The present invention relates to a field effect transistor using an organic semiconductor layer having crystal grains and a method of Manufacturing the field effect transistor.

BACKGROUND ART

The nonlinear optical characteristics, conductivity, and semiconductivity of an organic semiconductor compound have attracted attention in the field of optoelectronics, so that the development of various devices has been vigorously conducted.

In recent years, a field effect transistor (FET) element using an organic semiconductor compound for its semiconductor layer has been attracting attention. In view of this circumstance, an organic semiconductor compound is now considered to be suitable for the preparation of a flexible element using plastics as its substrate because the organic semiconductor compound exhibits flexible film property as compared to an inorganic material such as silicon.

Representative examples of such an organic semiconductor compound include phthalocyanine-based compounds and polyacenes. Characteristics such as nonlinear optical characteristics, conductivity, and semiconductivity necessary for preparing devices using those compounds as organic materials are known to largely depend on the crystallinity and orientation of the materials as well as their purities. However, it has been difficult to make many compounds such as the phthalocyanine-based compound and the polyacenes mentioned earlier, in which π-conjugated systems are extended, highly pure partly because the compounds are insoluble in solvents and susceptible to oxidation in the atmosphere. Moreover, a large-scale apparatus has been necessary for film formation partly because vacuum evaporation should be performed in order to obtain a crystallized film having high orientation.

For instance, pentacene, a representative example of an organic semiconductor compound, can be formed into a film on a substrate by means of vacuum evacuation alone because pentacene has high crystallinity and is insoluble in a solvent.

Meanwhile, an FET is prepared more simply by forming a thin film using a solution of an organic semiconductor that is soluble in an organic solvent by means of a coating method such as a spin coating method. Examples of such a FET include one using a π-conjugated polymer for its semiconductor layer (see "Japanese Journal of Applied Physics," Japan Society of Applied Physics, vol. 30, pp. 596-598, 1991). It is known that, in the case of a π-conjugated polymer, an arrangement state of molecular chains largely affect electric conductive characteristics. Similarly, it has been reported that a field effect mobility (hereinafter, referred to as "mobility") of a π-conjugated polymer field effect transistor is largely dependent on the arrangement state of the molecular chains in the semiconductor layer (see "Nature," Nature Publishing Group, vol. 401, pp. 685-687, 1999).

However, the arrangement of the molecular chains of a π-conjugated polymer is performed during a period from solution coating to solution drying. Therefore, there is a possibility that the arrangement state of the molecular chains varies to a large extent owing to an environmental change or depending on coating method. In view of this, there has been reported an FET using a film obtained by: forming a thin film of a soluble precursor of pentacene through coating; and subjecting the thin film to heat treatment to transform the precursor into pentacene (see "Advanced Materials," WILEY-VCH Verlag GmbH, vol. 11, pp. 480-483, 1999). In this case, the transformation into pentacene necessitates high-temperature treatment, and an eliminated component having a large mass must be removed under reduced pressure.

DISCLOSURE OF THE INVENTION

As described above, a conventional FET element using an organic semiconductor compound has followed a complicated step such as vacuum film formation to form a semiconductor layer having crystallinity.

The present invention has been made in order to solve the problems involved in the background art, and therefore an object of the present invention is to provide a field effect transistor which enables formation of an organic semiconductor layer having high crystallinity by a method much simpler than a conventional method, and which exhibits a high mobility, and to provide a method of manufacturing the field effect transistor.

According to one aspect of the present invention, there is provided a field effect transistor having an organic semiconductor layer, in which crystal grains having a maximum diameter of 10 μm or more account for 25% or more of a surface area of the organic semiconductor layer.

In further aspect of the field effect transistor, the organic semiconductor layer contains 7 to 200 crystal grains having a maximum diameter of 10 μm or more per 0.01 $mm^2$.

In further aspect of the field effect transistor, the organic semiconductor layer contains a porphyrin crystal.

According to another aspect of the present invention, there is provided a method of manufacturing a field effect transistor having an organic semiconductor layer, including the step of forming the organic semiconductor layer containing crystal grains having a maximum diameter of 10 μm or more, the crystal grains accounting for 25% or more of a surface area of the organic semiconductor layer, in which the step of forming the organic semiconductor layer includes transforming a thin film of an organic semiconductor compound precursor into a thin film of an organic semiconductor compound.

In further aspect of the method of manufacturing a field effect transistor, the organic semiconductor compound precursor is a precursor of a crystalline porphyrin compound.

According to the present invention, there can be provided a field effect transistor which has an organic semiconductor layer having high crystallinity, and which exhibits a high mobility.

In addition, according to the present invention, there can be provided a method of manufacturing a field effect transistor exhibiting a high mobility, with which an organic semiconductor layer having high crystallinity can be formed much simply than a conventional method.

BEST MODE FOR CARRYING OUT THE INVENTION

Figure 1:
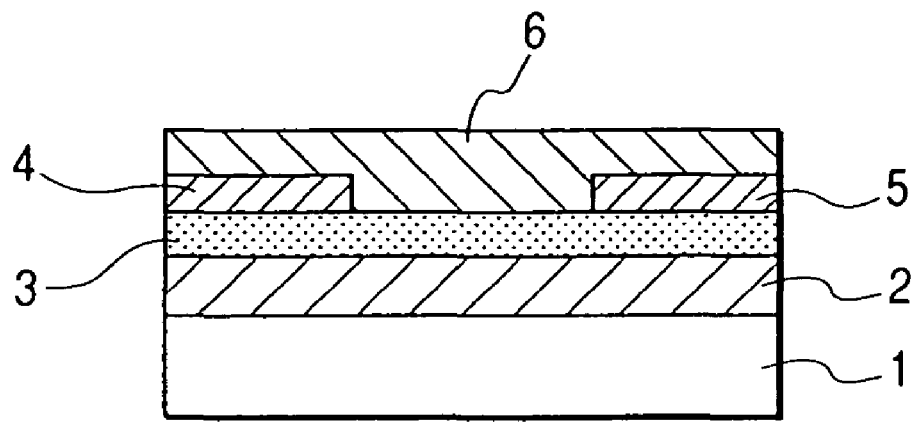
FIG. 1 is an enlarged schematic diagram of a part of a field effect transistor of the present invention.

Hereinafter, an embodiment of the present invention will be described in detail.

A field effect transistor of the present invention is characterized in that the field effect transistor has an organic semiconductor layer, and crystal grains having a maximum diameter of 10 μm or more account for 25% or more of the surface area of the organic semiconductor layer. Furthermore, the field effect transistor is characterized in that the organic semiconductor layer contains 7 to 200 crystal grains having a maximum diameter of 10 μm or more per 0.01 mm$^2$.

In order for the field effect transistor of the present invention to exhibit a high field effect mobility, it is important that the organic semiconductor layer has crystallinity. In particular, the growth of crystal grains is observed in an organic semiconductor layer having an average thickness of 10 to 200 nm. The term "average thickness" as used herein refers to an average value for film thicknesses measured by using a surface roughness tester, a step-difference measuring apparatus, or the like. It is not required that the thickness of the organic semiconductor layer be uniform. The average thickness is preferably 20 to 100 nm because the crystal grains grow to a larger extent to provide a high field effect mobility.

Crystal grains in an organic semiconductor layer can be observed with a light microscope or the like from a direction perpendicular to a substrate. The surface shape of the crystal grains can also be observed with an atomic force microscope (AFM) or the like. The shape of the crystal grains observed with a light microscope is a circular shape, an elliptical shape, a polygonal shape, a needle-like shape, a branched shape, or the like, so that the maximum diameter of the observed crystal grains can be measured. When the surface of the organic semiconductor layer is observed with a light microscope, the length of the longest line out of the lines, each of which is obtained by connecting two arbitrary points on a grain boundary between a crystal grain appearing on the surface of the organic semiconductor layer and an adjacent crystal grain, or on a boundary between the crystal grain appearing on the surface of the organic semiconductor layer and a noncrystalline portion, is defined as the maximum diameter of the crystal grains.

Only crystal grains having a maximum diameter of 10 μm or more can be selected form an image taken with a light microscope to determine the maximum diameter of the crystal grains. The maximum diameter of the crystal grains is preferably 10 to 70 μm. When the organic semiconductor layer contains 7 to 200, preferably 7 to 100 crystal grains having a maximum diameter of 10 μm or more per 0.01 mm$^2$, the field effect transistor of the present invention exhibits a high field effect mobility. The number of crystal grains per 0.01 mm$^2$ can be measured through observation with a light microscope or the like as in the case of the maximum diameter. When the surface of the organic semiconductor layer is observed with a light microscope or the like and crystal grains having a maximum diameter of 10 μm or more account for 25% or more, preferably 40% or more of the surface area of the organic semiconductor layer, the field effect transistor of the present invention exhibits a high field effect mobility.

When the field effect transistor of the present invention is observed with a light microscope, a portion occupied by crystal grains having a maximum diameter of 10 μm or more can be clearly distinguished from the other portion, and an arbitrary position can be preserved as an image such as a photograph. Large crystal grains having a maximum diameter of 10 μm or more can be easily distinguished on an image. Therefore, those crystal grains can be subjected to image processing to calculate the area of a portion occupied by large crystal grains having a maximum diameter of 10 μm or more and the area of the other portion. A ratio of the area of the organic semiconductor layer surface accounted for by crystal grains having a maximum diameter of 10 μm or more can be deduced from the areas.

There is a strong possibility that crystal grains having a maximum diameter of less than 10 μm, a microcrystalline portion, and a noncrystalline portion serve as barriers to the movement of a carrier in the organic semiconductor layer. The crystal grains having a maximum diameter of less than 10 μm, the microcrystalline portion, and the noncrystalline portion may be responsible for a reduction in mobility of the field effect transistor of the present invention if they widely extend over the organic semiconductor layer. However, when the above conditions are met, even if crystal grains having a maximum diameter of less than 10 μm, a microcrystalline portion, and a noncrystalline portion are coexistent, the field effect transistor of the present invention exhibits a high field effect mobility.

Examples of an organic semiconductor compound allowed to be present in the organic semiconductor layer include: polyacenes such as pentacene; low-molecular-weight compounds such as phthalocyanines, porphyrins, oligothiophenes, and oligofluorenens; and π-conjugated polymers such as polythiophene, polyfluorene, and polyphenylene vinylene. However, the organic semiconductor compound is not limited to those compounds. The organic semiconductor compound is preferably porphyrin. In particular, a field effect transistor using an organic semiconductor layer containing a porphyrin crystal exhibits a high field effect mobility.

A method of manufacturing a field effect transistor of the present invention is characterized by including the step of forming the organic semiconductor layer by transforming a thin film of an organic semiconductor compound precursor into an organic semiconductor compound. The term "organic semiconductor compound precursor" used herein refers to a compound which can be transformed into an organic semiconductor compound through heat treatment or the like in yield of 99% or more. Examples of a method of transforming an organic semiconductor compound precursor into an organic semiconductor compound include: heat treatment; and irradiation with radiation such as a laser or ultraviolet light. However, the simplest method is heat treatment.

The organic semiconductor compound precursor is preferably a compound that can be dissolved in various kinds of organic solvents. Application of various purification methods to a solution of the organic semiconductor compound precursor provides a highly pure organic semiconductor-compound. In addition, the organic semiconductor compound precursor is preferably a compound a solution of which can be applied to a substrate to form a noncrystalline and uniform coating film in contrast to an organic semiconductor compound having high crystallinity to form a crystal grain. In this case, an organic semiconductor layer can be formed over a large area for a short period of time by means of any of the coating methods such as a spin coating method, various printing methods, a dropping method, and a dipping method, which are simpler than evaporation and the like.

Examples of the organic semiconductor compound precursor that can be transformed into an organic semiconductor compound include precursors of pentacene, porphyrin, and polyphenylene vinylene. However, the organic semiconductor compound precursor is not limited to those precursors. Of those, a porphyrin precursor is preferable because of its solubility in an organic solvent and uniformity of a coating film. Examples of the porphyrin precursor include bicycloporphyrin compounds represented by the following general formulae (1) and (2).

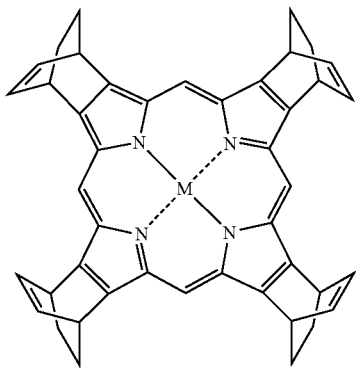

(1)

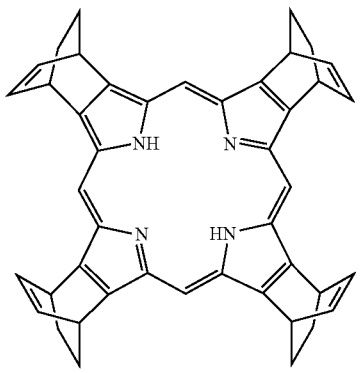

(2)

(In the formula (1), M represents a metal atom or a metal oxide.)

Each of the bicycloporphyrin compounds listed here (hereinafter, referred to as bicyclo compounds) is soluble in an organic solvent by virtue of the steric effect of its four bicyclo rings, and a coating film made from a solution of the bicyclo compound through coating has high thickness uniformity and is amorphous. The bicyclo rings of the bicyclo compound are each decomposed into ethylene, which is volatile, and a benzene ring through heat treatment to transform the bicyclo compound into tetrabenzo porphyrin compounds (hereinafter referred to as, benzo compounds) represented by the following general formulae (3) and (4). A benzo compound, which has an elongated conjugated system and increased planarity as compared to a bicyclo compound, forms a crystal grain in a thin film, which is a solid, to provide an organic semiconductor layer having the crystal grain.

As a result, a field effect transistor exhibiting a high field effect mobility can be obtained.

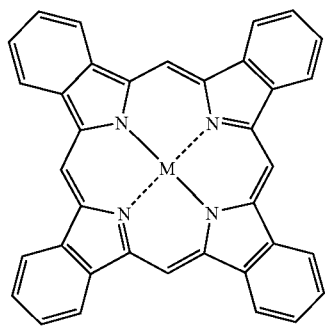

(3)

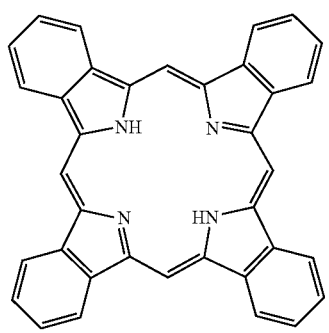

(4)

(In the formula (3), M represents a metal atom or a metal oxide.)

Next, the structure of the field effect transistor of the present invention and a method of manufacturing the field effect transistor will be described.

Figure 2:
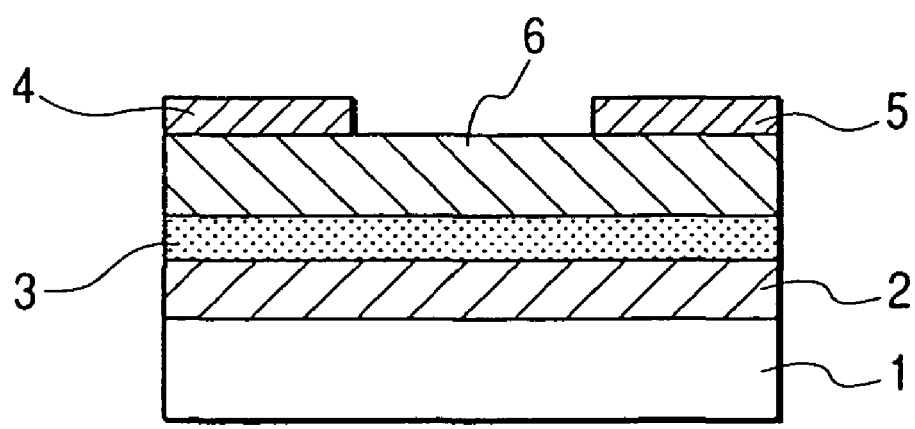
FIG. 2 is an enlarged schematic diagram of a part of a field effect transistor of the present invention.
Figure 3:
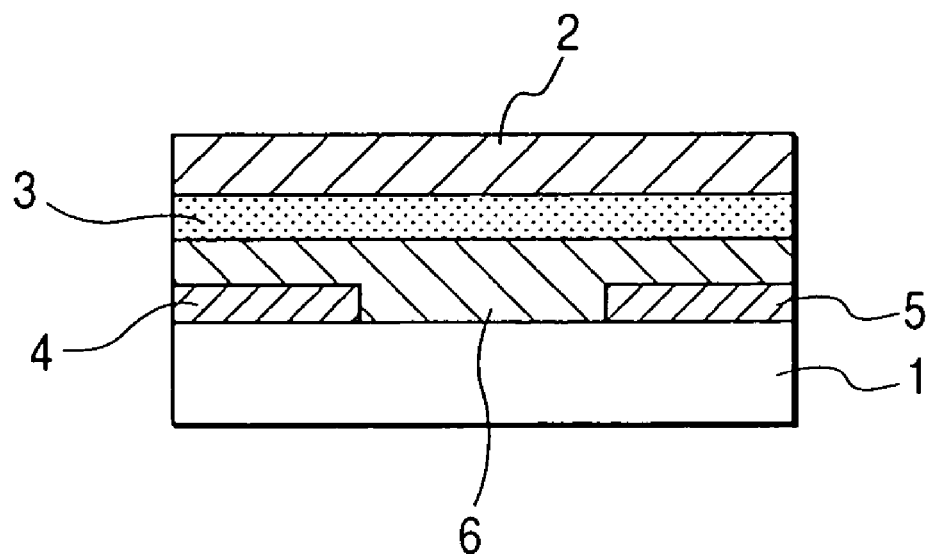
FIG. 3 is an enlarged schematic diagram of a part of a field effect transistor of the present invention.

FIG. 1, FIG. 2, and FIG. 3 are each an enlarged schematic diagram of a part of the field effect transistor of the present invention.

As shown in each of the figures, the field effect transistor of the present invention is constituted of a substrate 1, a gate electrode 2, a gate insulating layer 3, a source electrode 4, a drain electrode 5, and an organic semiconductor layer 6.

A substrate obtained by processing an inorganic material such as Si, glass, or metal, or a resin material such as polyethylene terephthalate (PET), polyethylene naphthalate (PEN), polyimide (PI), polyetherimide (PEI), polyethersulfone (PES), polysulfone (PSF), polyphenylene sulfide (PPS), polyetheretherketone (PEEK), polyarylate (PAR), or polyamideimide (PAI) into a plate or a sheet can be used as the substrate 1. In preparing a flexible element, a resin substrate is preferably used. In forming an organic semiconductor layer through heat treatment, an inorganic substrate or a heat-resistant resin substrate made of polyimide or the like is used.

The gate electrode 2 is not particularly limited as long as the electrode is made of a conductive material. Examples of such a conductive material include: platinum, gold, silver, nickel, chromium, copper, iron, tin, antimonial lead, tantalum, indium, aluminum, zinc, and magnesium, and alloys thereof; conductive metal oxides such as an indium tin oxide; and inorganic and organic semiconductors with conductivities increased by doping or the like such as a silicon single crystal, polysilicon, amorphous silicon, germanium, graphite, polyacetylene, polyparaphenylene, polythiophene, polypyrrole, polyaniline, polythienylene vinylene, and polyparaphenylene vinylene. Examples of a method of preparing an electrode include a sputtering method, an evaporation method, a printing method using a solution or paste, and an ink jet method.

Any gate insulating layer can be used as the gate insulating layer 3 as long as a uniform organic semiconductor layer can be formed. However, a gate insulating layer having a high dielectric constant and a low conductivity is preferable. Examples of an insulating material for such an insulating layer include: inorganic oxides and nitrides such as silicon oxide, silicon nitride, aluminum oxide, titanium oxide, and tantalum oxide; and organic polymers such as polyacrylate, polymethacrylate, polyethylene terephthalate, polyimide, polyether, and a siloxane-containing polymer. In addition, of the above insulating materials, an insulating material having high surface smoothness is preferable.

The source electrode 4 and the drain electrode 5 are not particularly limited as long as the electrodes are made of the same conductive material as that of the gate electrode 2. An electrode material having a low electrical resistance at a contact surface with the semiconductor layer is preferable as an electrode material for the electrodes.

As described above, an organic semiconductor compound precursor is preferably used for the organic semiconductor layer 6. A method of preparing an organic semiconductor layer is described as an example. An organic semiconductor compound precursor is dissolved into an organic solvent, and the solution is applied to a substrate and then dried. After that, the dried product is subjected to heat treatment to form the organic semiconductor layer 6.

An organic solvent used for dissolving an organic semiconductor compound precursor is not particularly limited as long as the solvent does not react with the solute and the solute is not precipitated in the organic solvent. In addition, two or more kinds of organic solvents may be mixed. The concentration of the solution, which is arbitrarily adjusted depending on a desired film thickness, is preferably 0.01 to 5 wt %.

Examples of a coating method include a spin coating method, a dipping method, a dropping method, an offset, screen, and other printing methods, and an ink jet method. In addition, it is desirable to filter the solution through a membrane filter in advance in order to minimize the mixing of foreign material or the like into a semiconductor layer. This is because the mixing of insoluble matter or foreign material from the outside prevents uniform orientation, thereby causing an increase in off-state current or a reduction in on/off ratio. In addition, the coating film can be predried at a temperature equal to or lower than 120° C.

The transformation of the coated and formed organic semiconductor compound precursor film into an organic semiconductor compound film is preferably performed through heat treatment. The heat treatment is performed by keeping a heat treatment temperature at a temperature higher than a temperature at which the transformation starts (transformation starting temperature) by 20 to 120° C., preferably 30 to 110° C. for 10 to 900 seconds although the heat treatment temperature varies depending on the kind of a reaction occurring upon the transformation and a structural change. In this case, a transformation rate is fast, so that crystal growth is promoted to thereby result in an organic semiconductor layer having a large number of crystal grains having a larger maximum diameter. The transformation starting temperature can be determined by thermal analysis or a change in ultraviolet-visible spectrum or in infrared absorption spectrum depending on a heating temperature and over time. A heat treatment temperature lower than the transformation starting temperature +20° C. reduces the transformation rate and prolongs a heat treatment time period, so that crystal grains cannot be sufficiently large. On the other hand, a heat treatment temperature in excess of the transformation starting temperature +120° C. is not preferable because a crack develops owing to abrupt film contraction, leading to a reduction in mobility.

In the case where any one of the bicycloporphyrin compounds (hereinafter referred to as bicyclo compounds) is used as the organic semiconductor compound precursor, the film of the bicyclo compound is heated to cause an elimination of $CH_2$=$CH_2$ due to a retro Diels-Alder reaction, thereby undergoing a transformation into a benzo porphyrin compound (hereinafter referred to as benzo compound). Crystal growth occurs owing to the stacking of the porphyrin rings of the produced benzo compound, and hence the organic semiconductor layer 6 having crystal grains is obtained. Since the transformation starting temperature of a bicyclo compound is around 150° C., a heating temperature for obtaining a higher field effect mobility is preferably 170 to 250° C.

As a heat treatment method, the heating of the film is performed on a hot plate, or in an oven with internal air circulation or a vacuum oven. It is preferable to instantaneously heat the film on a hot plate in order to obtain an organic semiconductor layer which is uniform and has higher orientation.

A field effect transistor structure in the present invention may be any one of a top contact electrode type shown in FIG. 1, a bottom contact electrode type shown in FIG. 2, and a top gate electrode type shown in FIG. 3. In addition, the field effect transistor structure in the present invention is not limited to a thin film type but may be a stereo type.

Synthesis examples and examples are shown below. However, the present invention is not limited to these examples.

SYNTHESIS EXAMPLE 1

Synthesis of Bicyclo Compound

Step (1)

A mixed solution of 3.16 g (39.5 mmol) of 1,3-cyclohexadiene, 10.5 g (34.05 mmol) of trans-1,2-bis(phenylsulfonyl)ethylene, and 200 ml of toluene was refluxed for 7 hours. Then, the mixed solution was cooled and concentrated under reduced pressure to yield a reaction mixture. The reaction crude product was recrystallized (chloroform/hexane) to yield 5,6-bis(phenylsulfonyl)-bicyclo[2,2,2]octa-2-ene (13.8 g, 35.6 mmol, 90% yield).

Step (2)

A reaction system of a mixed solution of 7.76 g (20 mmol) of the resultant 5,6-bis(phenylsulfonyl)-bicyclo[2,2,2]octa-2-ene and 50 ml of anhydrous tetrahydrofuran was replaced with nitrogen. Then, 2.425 ml (22 mmol) of ethyl isocyanoacetate were added to the mixed solution, and the whole was cooled to 0° C. Potassium tert-butoxide (50 ml/1 M THF solution) was dropped into the mixture in 2 hours, and the whole was stirred at room temperature for 3 hours. After the completion of the reaction, diluted hydrochloric acid was added to the reaction mixture. Then, the reaction mixture was washed with a saturated aqueous solution of sodium hydrogen carbonate, distilled water, and a saturated aqueous solution in this order, and was dried with anhydrous sodium sulfate. The dried product was purified by means of silica gel column chromatography (chloroform) to yield ethyl-4,7-dihydro-4,7-ethano-2H-isoindole-1-carboxylate (3.5 g, 16 mmol, 80% yield).

Step (3)

Under an argon atmosphere, a mixed solution of 0.42 g (1.92 mmol) of the resultant ethyl-4,7-dihydro-4,7-ethano-2H-isoindole-1-carboxylate and 50 ml of anhydrous THF was cooled to 0° C. Then, 0.228 g (6 mmol) of lithium aluminum hydride powder was added to the mixed solution, and the whole was stirred for 2 hours. After that, THF was removed, and then the remainder was extracted with chloroform, washed with a saturated aqueous solution of sodium hydrogen carbonate, distilled water, and a saturated salt solution in this order, and dried with anhydrous sodium sulfate. The reaction solution was filtered, replaced with argon, and shaded. Then, 10 mg of p-toluenesulfonic acid were added to the reaction solution, and the whole was stirred for 12 hours at room temperature. Furthermore, 0.11 g of p-chloranil was added to the mixture, and the whole was stirred for 12 hours at room temperature. The resultant was washed with a saturated aqueous solution of sodium hydrogen carbonate, distilled water, and a saturated aqueous solution in this order, and dried with anhydrous sodium sulfate. After the concentration of the solution, the concentrated product was subjected to alumina column chromatography (chloroform) and recrystallized (chloroform/methanol) to yield a metal-free bicyclo compound (bicycloporphyrin) represented by the following structural formula (5) (0.095 g, 0.096 mmol, 20% yield).

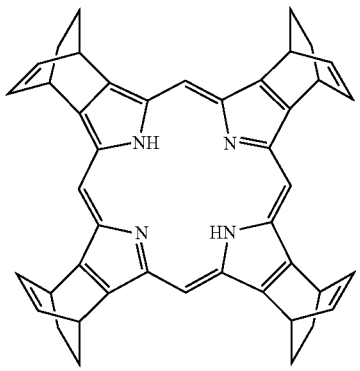

(5)

Step (4)

A solution of 0.020 g (0.032 mmol) of bicycloporphyrin and 0.019 g (0.1 mmol) of copper(II) acetate monohydrate in a mixture of 30 ml of chloroform and 3 ml of methanol was stirred at room temperature for 3 hours. The reaction solution was washed with distilled water and a saturated aqueous solution, and was then dried with anhydrous sodium sulfate. After the concentration of the solution, the concentrated product was recrystallized with chloroform/methanol to yield a bicycloporphyrin copper complex represented by the following structural formula (6) (0.022 g, 100% yield).

The temperature at which the transformation of the bicycloporphyrin copper complex into a benzo body starts was measured with a thermogravimetry apparatus Thermoplus TG8120 (trade name) manufactured by Rigaku Corporation under a nitrogen atmosphere at a rate of temperature increase of 10° C./min. The transformation starting temperature measured was 140° C.

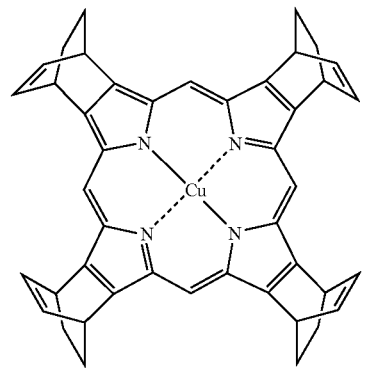

(6)

EXAMPLE 1

Figure 4:
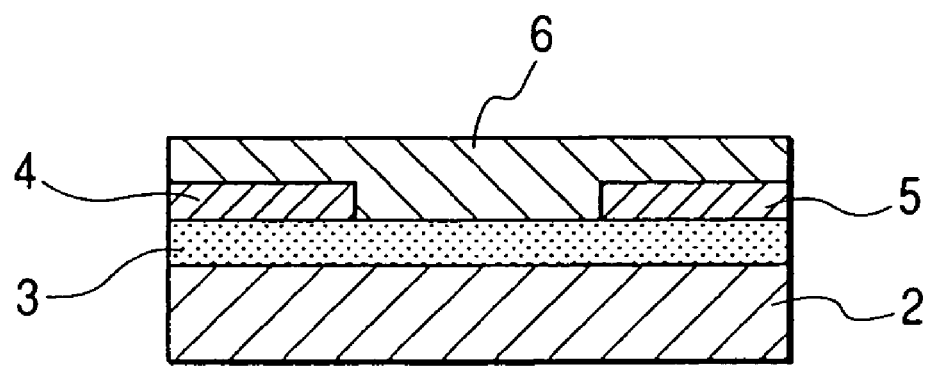
FIG. 4 is an enlarged schematic diagram of a part of a field effect transistor of the present invention.

FIG. 4 shows the structure of a bottom gate type field effect transistor in this example.

First, a highly doped N-type silicon substrate was provided as the gate electrode 2. A silicon oxide film of 5,000 Å in thickness obtained by thermal oxidation of the silicon substrate surface layer was provided as the gate insulating layer 3. Chromium and gold were deposited from the vapor in this order onto the gate insulating layer 3 to form the source electrode 4 and the drain electrode 5 by means of an ordinary photolithography technique. Subsequently, the substrate surface was treated with ozone. Then, a coating film made from a 1 wt % chloroform solution of the bicycloporphyrin copper complex synthesized in Synthesis Example 1 was formed on the substrate by means of a spin coating method. Furthermore, the substrate was heated on a hot plate at 220° C. to form the organic semiconductor layer 6 composed of a benzo compound represented by the following structural formula (7). It was confirmed that the transformation into the benzo compound was completed in 480 seconds.

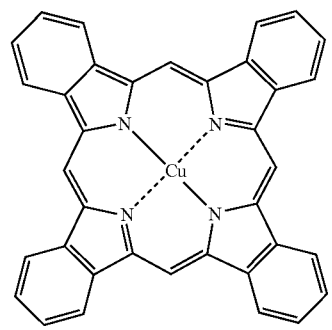

(7)

The organic semiconductor layer had an average thickness of 50 nm. The transistor surface was observed with a light microscope to find an elliptical crystal grain. Furthermore, the number n of crystal grains having a maximum diameter of 10 μm or more per 0.01 mm² and a share S (%) of the crystal grains on the channel were 24 and 63%, respectively.

Figure 5:
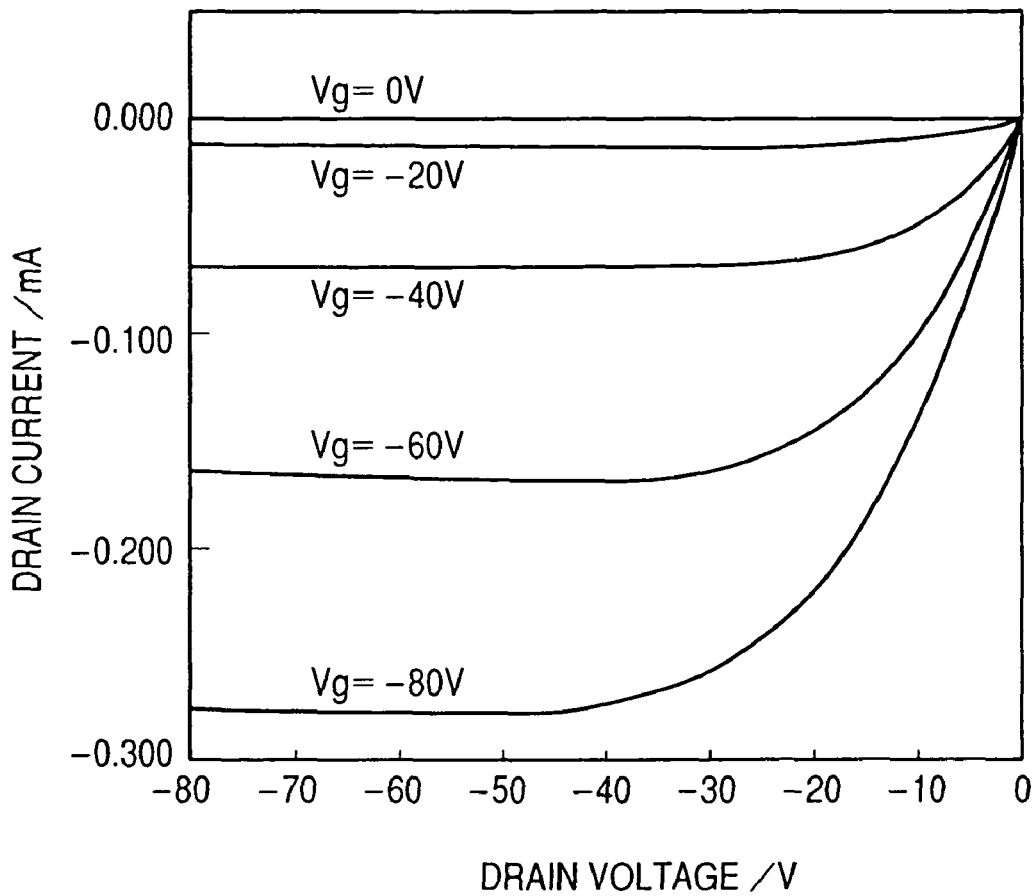
FIG. 5 shows electrical characteristics of a field effect transistor in Example 1 of the present invention.

A field effect transistor having a channel length L of 50 μm and a channel width W of 10 mm was prepared according to the above procedure. The $V_d$-$I_d$ and $V_g$-$I_d$ curves of the prepared transistor were measured by using a Parameter Analyzer 4156C (trade name) manufactured by Agilent, to thereby provide results shown in FIG. 5.

A mobility at room temperature and in the atmosphere was calculated from the following equation (1).

$$\text{Mobility } \mu = (V_g - \sqrt{(\text{gradient of } I_d \text{ in linear region})})^2 \times (1/C_i) \times (L/2W) \quad \text{(Eq. 1)}$$

In the equation, μ denotes a mobility (cm$^2$/Vs) and $C_i$ denotes a capacitance of the gate insulating film (F/cm$^2$). W and L denote the channel width (mm) and the channel length (μm) described in this example, respectively. In addition, $V_g$ denotes a gate voltage (V) and $I_d$ denotes a drain current (A).

In addition, the on/off ratio was determined from a ratio of $I_d$ at $V_g$=80 V to $I_d$ at $V_g$=0 V. Table 1 shows the results.

EXAMPLE 2

Operations similar to those of Example 1 were performed except that the channel length L and the channel width W were changed to 50 μm and 2 mm, respectively. Table 1 shows the results.

EXAMPLE 3

Operations similar to those of Example 1 were performed except that the field effect transistor structure was changed to a top electrode type as described below.

Figure 6:
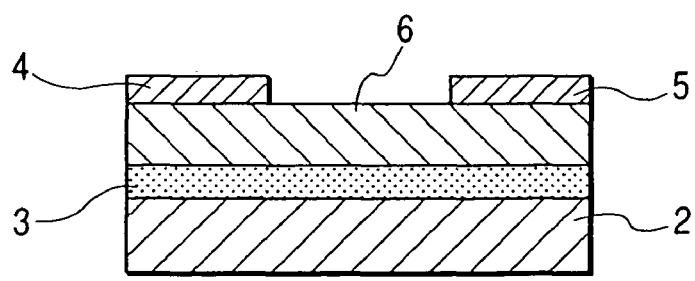
FIG. 6 is an enlarged schematic diagram of a part of a field effect transistor of the present invention.

FIG. 6 shows the structure of a top gate type field effect transistor.

First, a highly doped N-type silicon substrate was provided as the gate electrode 2. A silicon oxide film of 5,000 Å in thickness obtained by thermal oxidation of the silicon substrate surface layer was provided as the gate insulating layer 3. Subsequently, the substrate surface was treated with ozone. Then, a coating film made from a 1 wt % chloroform solution of the bicyclo compound synthesized in Synthesis Example 1 was formed on the substrate by means of a spin coating method. Furthermore, the substrate was heated on a hot plate at 220° C. to form the organic semiconductor layer 6 composed of a benzo compound. It was confirmed that the transformation into the benzo compound was completed in 480 seconds.

The organic semiconductor layer on the substrate had an average thickness of 50 nm. A circular crystal grain was observed with a light microscope. The number n of crystal grains having a maximum diameter of 10 μm or more per 0.01 mm$^2$ and a share S (%) of the crystal grains on the channel were 21 and 57%, respectively. Chromium and gold were deposited from the vapor in this order onto the organic semiconductor layer 6 to form the source electrode 4 and the drain electrode 5 with a channel length L of 50 μm and a channel width W of 10 mm by means of an ordinary photolithography technique. Table 1 shows the results.

EXAMPLE 4

Operations similar to those of Example 1 were performed except that the heating temperature was changed to 200° C. It was confirmed that the transformation into the benzo compound was completed in 600 seconds. An elliptical crystal grain was observed with a light microscope. Table 1 shows the results.

COMPARATIVE EXAMPLE 1

Operations similar to those of Example 1 were performed except that the heating temperature was changed to 155° C. The transformation into the benzo compound was completed in 1,800 seconds. Elliptical and needle-like crystal grains were observed with a light microscope. Table 1 shows the results.

COMPARATIVE EXAMPLE 2

Operations similar to those of Example 1 were performed except that the heating temperature was changed to 140° C. The transformation into the benzo compound was completed in 3,600 seconds. A needle-like crystal grain was observed with a light microscope. Table 1 shows the results.

TABLE 1

| | W (mm)/ L (μm) | Mobility (cm$^2$/Vs) | Heating temperature (C.°)/Time (sec) | ON/OFF ratio | Thickness (μm) | n | Share(%) |
|---|---|---|---|---|---|---|---|
| Example 1 | 10/50 | 0.09 | 220/480 | $1.5 \times 10^4$ | 50 | 24 | 63 |
| Example 2 | 2/50 | 0.09 | 220/480 | $1.3 \times 10^4$ | 50 | 27 | 65 |
| Example 3 | 10/50 | 0.10 | 220/480 | $1.9 \times 10^4$ | 50 | 21 | 57 |
| Example 4 | 10/50 | 0.02 | 200/600 | $3.6 \times 10^4$ | 50 | 30 | 45 |
| Comparative Example 1 | 10/50 | $5 \times 10^{-5}$ | 155/1,800 | 50 | 55 | 8 | 4 |
| Comparative Example 2 | 10/50 | $1 \times 10^{-5}$ | 140/3,600 | 20 | 55 | 3 | <1 |

The field effect transistor of the present invention can be used for various devices in the fields of organic electronics and optoelectronics because the transistor has an organic semiconductor layer having high crystallinity and exhibits a high mobility.

In addition, with the method of manufacturing a field effect transistor of the present invention, an organic semiconductor layer having high crystallinity can be formed much simply than a conventional method, and the method can be used for manufacturing a field effect transistor exhibiting a high field effect mobility.

This application claims priority from Japanese Patent Application No. 2003-305485 filed on Aug. 28, 2003, where is hereby incorporated by reference herein.

The invention claimed is:

1. A method of forming an organic semiconductor layer for a field effect transistor, the organic semiconductor layer comprising a porphyrin copper complex compound, the method comprising the steps of:
   applying a solution containing a bicycloporphyrin copper complex compound to a substrate; and
   heating the substrate applied with the solution containing the bicycloporphyrin copper complex compound at a temperature of between 200° C. and 220° C. to form the organic semiconductor layer,
   wherein the bicycloporphyrin copper complex compound is a complex obtained by coordinating a copper atom with metal-free bicycloporphyrin, and the metal-free bicycloporphyrin is recrystallized and wherein the organic semiconductor layer contains crystal grains having a maximum diameter of at least 10 μm, the crystal grains accounting for at least 25% of a surface area of the organic semiconductor layer.

2. A method of forming an organic semiconductor layer for a field effect transistor according to claim 1, wherein the bicycloporphyrin copper complex compound is a compound represented by the following formula:

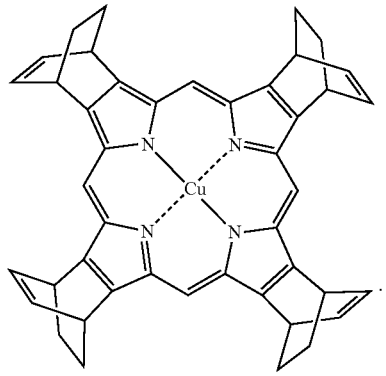

* * * * *